United States Patent [19]
Goldhardt et al.

[11] Patent Number: 5,411,491
[45] Date of Patent: May 2, 1995

[54] LOW PROFILE GASTROSTOMY DEVICE WITH ONE-WAY CROSS-SLIT VALVE

[75] Inventors: Donald J. Goldhardt, Grove City; William H. Hirsch, Columbus, both of Ohio

[73] Assignee: Abbott Laboratories, Abbott Park, Ill.

[21] Appl. No.: 69,035

[22] Filed: May 28, 1993

[51] Int. Cl.⁶ .............................. A61M 5/00
[52] U.S. Cl. ..................... 604/247; 604/256; 604/27; 604/332; 604/335
[58] Field of Search ............ 604/27, 28, 30, 34, 604/9, 167, 247, 256, 332, 335

[56] References Cited

U.S. PATENT DOCUMENTS

| | | |
|---|---|---|
| 2,230,226 | 2/1941 | Auzin . |
| 2,649,092 | 8/1953 | Wallace . |
| 2,687,131 | 8/1954 | Raiche . |
| 3,154,077 | 10/1964 | Cannon . |
| 3,253,594 | 5/1966 | Matthews et al. . |
| 3,812,841 | 5/1974 | Isaacson . |
| 3,915,171 | 10/1975 | Shermeta . |
| 3,961,632 | 6/1976 | Moosun . |
| 3,982,544 | 8/1976 | Dyck . |
| 4,315,513 | 2/1982 | Nawash et al. . |
| 4,393,873 | 7/1983 | Nawash et al. . |
| 4,416,273 | 11/1983 | Grimes . |
| 4,666,433 | 5/1987 | Parks . |
| 4,863,438 | 9/1989 | Gaurderer et al. . |
| 4,944,732 | 7/1990 | Russo . |
| 5,169,393 | 12/1992 | Moorehead et al. . |
| 5,201,722 | 4/1993 | Moorehead et al. . |
| 5,261,459 | 11/1993 | Atkinson et al. ............... 137/846 |
| 5,269,763 | 12/1993 | Boehmer et al. ............... 604/256 |
| 5,336,203 | 8/1994 | Goldhardt et al. ............... 604/27 |

OTHER PUBLICATIONS

Gauderer et al, "Feeding Gastrostomy Button: Experience and Recommendations", Journal of Pediatric Surgery, vol. 23, No. 1, pp. 24–28 (1988).
Goldhardt et al, Appln. Ser. No. 8/069,038, filed May 28, 1993 for "Low Profile Gastrostomy Device With Dome".

*Primary Examiner*—C. Fred Rosenbaum
*Assistant Examiner*—N. Kent Gring
*Attorney, Agent, or Firm*—Lonnie R. Drayer; Donald O. Nickey

[57] ABSTRACT

The one-way cross-slit valve of the invention is made of an elastomeric material and has a hollow cylindrical body with first and second ends and an axis and a passageway through the body, the passageway being entirely intercepted by a ridge and valley wall or web structure integrally joined to the cylindrical body. There are just two ridges in the form of lands that extend diametrically and intersect at a right angle at about the axis of the valve body and are slitted at the intersection to provide duckbill valve action. The ridges constitute the apices of mutually intersecting partially folded wall portions that are V-shaped in section, the V's spreading towards the first end where the intersecting walls join and form the valleys and the one-way action of the valve allowing fluid to move only towards the second end. The novel low profile gastrostomy tube combines a conventional dome and tubular shaft with the one-way cross-slit valve of the invention.

16 Claims, 8 Drawing Sheets

LOW PROFILE GASTROSTOMY DEVICE WITH ONE-WAY CROSS-SLIT VALVE

FIELD OF THE INVENTION

The invention relates to a gastrostomy device for insertion into a stoma in replacement of a gastrostomy device that has been removed intentionally or accidentally. It also relates to a novel cross-slit duckbill valve useful in the device as well as in other settings.

DESCRIPTION OF RELATED ART

Gastrostomies now assume a key role in the management of patients with swallowing difficulties due to injury or disease, as well as those patients requiring long term enteral feedings. In the most widely used gastrostomies of the recent past, access to the stomach has been had by a catheter, usually of the de Pezzer or Foley type. Although simple to use, these catheters have several disadvantages and are associated with a variety of complications, such as, internal or external migration, inadvertent removal, pivoting action leading to leakage and tissue reaction.

To overcome these problems rather simple skin-level silicone rubber devices have been developed which are designed to be inserted from the external or skin side into a stoma of an established gastrostomy. Each of these devices has a shaft in the form of a short tube or conduit extending from an inner bulb or dome, often of mushroom-like shape resembling the tip of a de Pezzer catheter, and with one or more perforations for liquid passage, to an external or outer portion that is self-retaining, e.g., with flat wings or a ridged or perforated flat flange. A valve, usually at the gastric opening of the shaft, prevents external reflux of intragastric contents. A small cap or plug at the skin level is removed and a simple hollow adapter is inserted into the shaft for feeding. The valve may have low opening pressure or the adapter may be inserted through the valve. Feeding accomplished, the tube or shaft is flushed with water, the adapter removed, and the cap or plug replaced.

U.S. Pat. No. 4,315,513 describes a gastrostomy or transport tube of the type referred to above, in this case with a check valve, i.e., a one-way valve, within the shaft with a valve stem attached to a hemispherical element that seats into a mating cavity when there is pressure within the stomach, with the valve stem extending through the bottom of the seat as a guide. In an alternative form of this device there is used a hemispherical bulb or dome of a soft rubber that is diametrically slit so that no internal check valve is needed. The wall of the bulb or dome is of uniform thickness similar to that of the wall of the shaft employed.

In U.S. Pat. No. 4,863,438 there is described a low profile gastrostomy device of the type referred to above with a hollow bulb-like internal retaining element with apertures for passage of fluids and with a flat flapper valve serving as a check valve. The flapper valve extends across the end of the shaft within the bulb-like retaining element. The bulb-like portion is of uniform wall thickness, the bottom portion being integrally formed with the shaft and the bottom portion being adhesively bonded to the top portion. The shaft at its outer or skin end is closed by a plug that is attached by a flexible membrane to the edge of one of the pair of flat wings or a flange that serves as the external retaining element.

In U.S. Pat. No. 4,944,732 there is described a device of the type referred to above that utilizes a hollow conical bulb or dome with at least one opening therethrough for passage of fluids and is of uniform wall thickness throughout. At the skin or feeding end, this device is provided with an externally threaded plug for closure, and, within the plug, a duckbill one-way slit valve that is removable during obturation or for decompression or for replacement thereof.

Each of the devices provided heretofore, while offering advances in the field, has suffered from certain drawbacks or problems, however. Significant problems have arisen from the one-way valves employed, which tend to be inefficient, i.e., leaky, from the start, or short-lived, or inconvenient to handle when decompression is necessary, or may require more pressure than desired to pass fluids therethrough. The valves also often interfere with the smooth elongation of the dome as needed when elongation with an obturator is done during insertion of the bulb or dome through the stoma and into the stomach. Or, the valve may have to be removed during use of the obturator, as, for example, the valves shown in U.S. Pat. No. 4,315,513 and U.S. Pat. No. 4,944,732.

SUMMARY OF THE INVENTION

The one-way valve of the invention is a cross-slit duckbill valve formed of an elastomeric material and having a foreshortened hollow cylindrical body with first and second ends and an axis and with the passageway through the cylindrical body entirely controlled by a transversely extending continuous ridge and valley web or wall structure with intersecting slits in a centrally located intersection of the ridges substantially at the axis. Within the cylindrical body the ridge and valley web consists of two wall portions, each partially folded along a line, the lines constituting the ridges or apices, each wall portion being V-shaped in section, and each wall portion extending substantially diametrically of the cylindrical body and normal to each other with the V's both opening in the same axial direction of the cylindrical body towards the first end thereof, and, with the lines formed by the apex of each folded wall portion meeting at about right angles to form four quadrants, each wall portion ending midway around a quadrant where it meets and merges with and is integrally joined to the mutually intersecting wall portion to form a valley extending radially outwardly from the intersection of the apices at about the axis of the cylindrical body as well as at an angle from the apices toward the direction of the first end of the cylindrical body, the so-shaped integral wall being a continuous wall of substantially uniform thickness formed within the confines of the cylindrical body and integrally formed therewith, the apices lying substantially in a common plane substantially diametric to the valve body and both being slit at the intersection of the two apices, forming the intersecting slits referred to above that extend entirely through the wall at the fold or land forming each apex, the apices facing toward the second end of the cylindrical body.

Typically the slits in valves used for medical devices such as a gastrostomy tube are about 1.5 to about 2.5 millimeters long, but may be somewhat longer or shorter when used in other settings with longer or shorter or wider or narrower or thicker or thinner lands. Preferably the apices are flattened in the form of lands. The slits are formed or cut through the lands longitudinally thereof.

The novel valve is advantageously used in a low profile gastrostomy tube having an apertured dome or bulb with a sidewall of uniform thickness and with the middle of the bottom wall thereof surrounding the inner end of a hollow tubular shaft and there being a retention flange, usually with a removable plug or other closure, connected to and surrounding the outer end of the tubular shaft. The valve may also be positioned at the outer end of the shaft, either adhesively bonded to the end of the shaft or mounted within an externally threaded shell that screws into an internally threaded well at the end of the shaft.

BRIEF DESCRIPTION OF THE PREFERRED EMBODIMENTS

Figure 11:
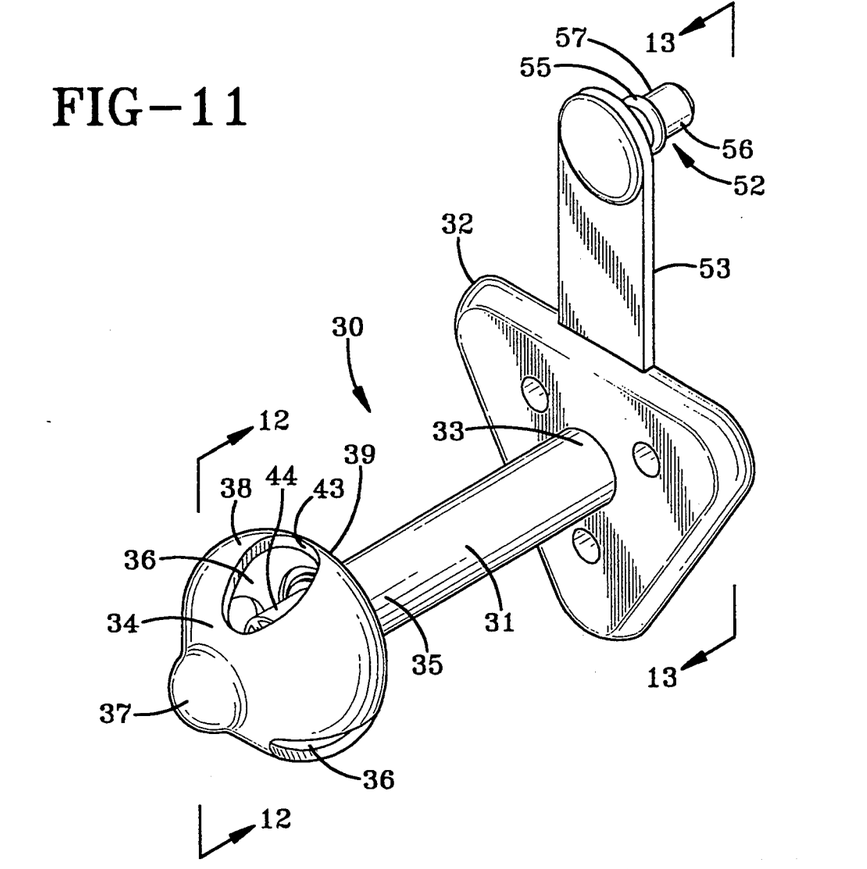
FIG. 11 is an isometric view of the novel low profile gastrostomy tube of the invention with a hollow tubular shaft with a retaining element and attached plug at one end and an apertured dome at the other.
Figure 12:
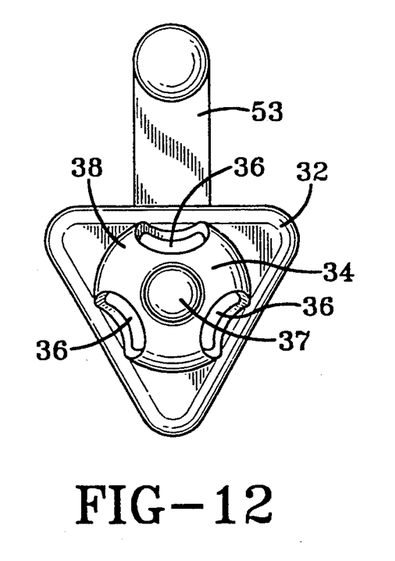
FIG. 12 is a view in front elevation of the novel gastrostomy tube taken along the lines 12—12 of FIG. 11.
Figure 13:
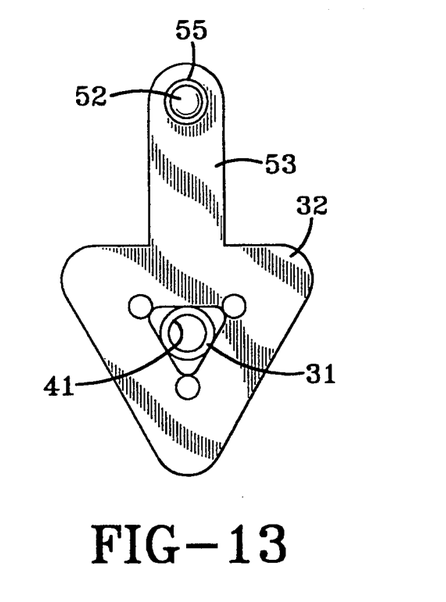
FIG. 13 is a view in rear elevation of the novel gastrostomy tube taken along the lines 13—13 of FIG. 11.

Referring now to FIGS. 11, 12 and 13, the novel low profile gastrostomy tube of the invention, indicated generally by the reference numeral 30, is seen to comprise a tubular shaft, or connector tube, 31 with a retention element or flange 32, sometimes referred to as a retention disc, at its outer end 33, and a conventional hollow, apertured dome 34 at its inward end 35, all formed of an elastomeric material, such as a silicone rubber. References herein to inner and outer end of the shaft are with reference to the disposition in the stoma of a patient. The elastomeric material may be a composition of most any elastomer that is medically acceptable for use in the stoma of a patient and has the ability to promptly recover its natural state or shape after being deformed. Silicone rubber and polyurethane are the preferred elastomers, with silicone rubber being most preferred; rubber latex and styrene-butadiene-rubber latex being less preferred.

Figure 1:
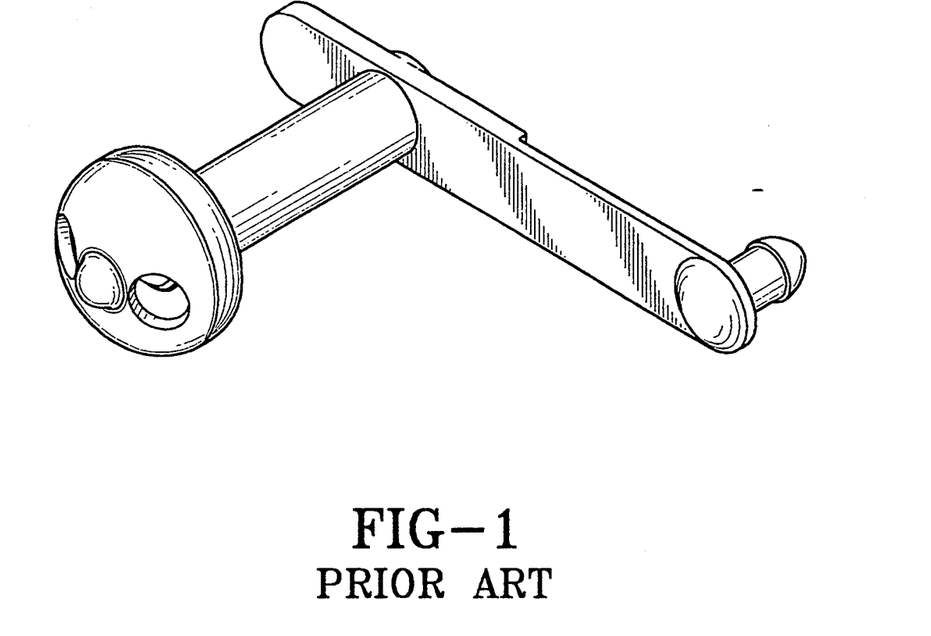
FIG. 1 is an isometric view of a low profile gastrostomy tube according to the prior art showing a hollow shaft with a perforated dome at the inner end of the shaft and with opposed wings or flanges at the outer end with a plug for the outer end of the shaft attached to one of the wings by a flexible membrane.
Figure 2:
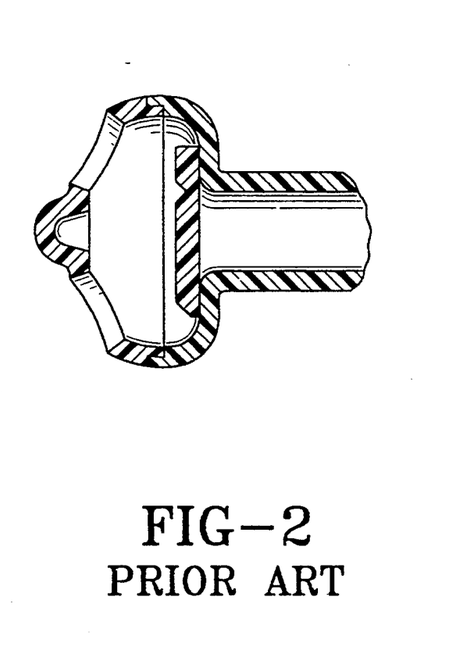
FIG. 2 is a fragmentary view in section of the dome and a portion of the inner end of the shaft of the device of FIG. 1 showing that the wall of the dome is of uniform thickness from apex to bottom wall, and, that there is within the dome a one-way flapper valve adapted to prevent the movement of any fluids out of the stomach into the shaft, and with the valve in the closed position.
Figure 3:
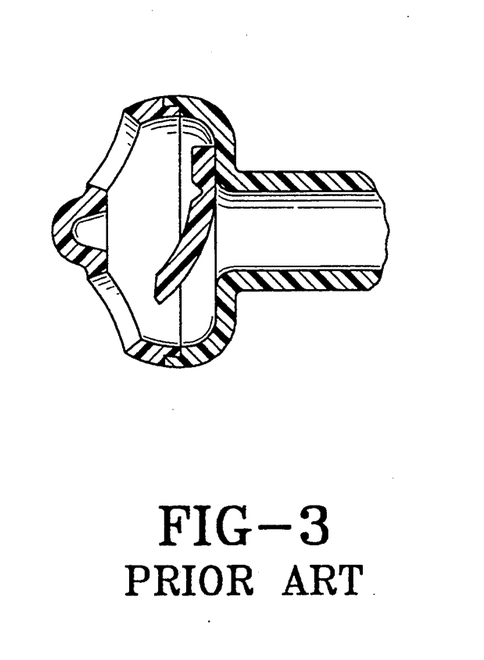
FIG. 3 is a fragmentary view like that of FIG. 2 showing the flapper valve in the open position as it would be when pushed partly open by an obturator or if pushed by a flow of feeding fluid. Such a valve may be defeated or rendered ineffective by tension placed on the dome, e.g., by patient weight gain thickening the body wall or by normal movement on the part of the patient.
Figure 4:
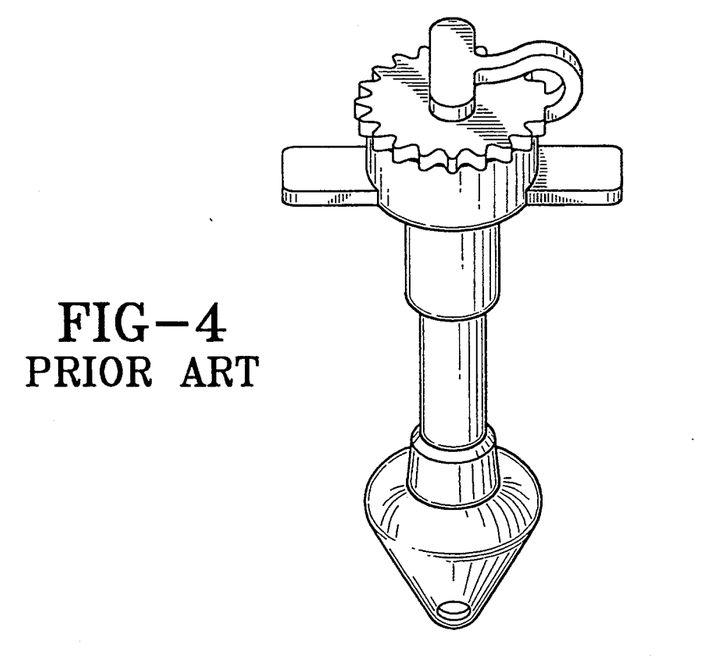
FIG. 4 is an isometric view of another form of gastrostomy tube according to the prior art showing a hollow shaft with a conical dome joined at the inner end of the shaft and with a closure of the shaft at the outer end thereof.
Figure 5:
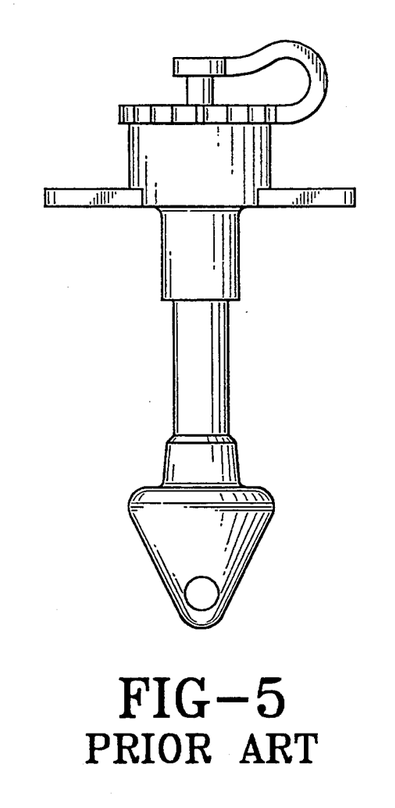
FIG. 5 is a view in side elevation of the device of FIG. 4.
Figure 14:
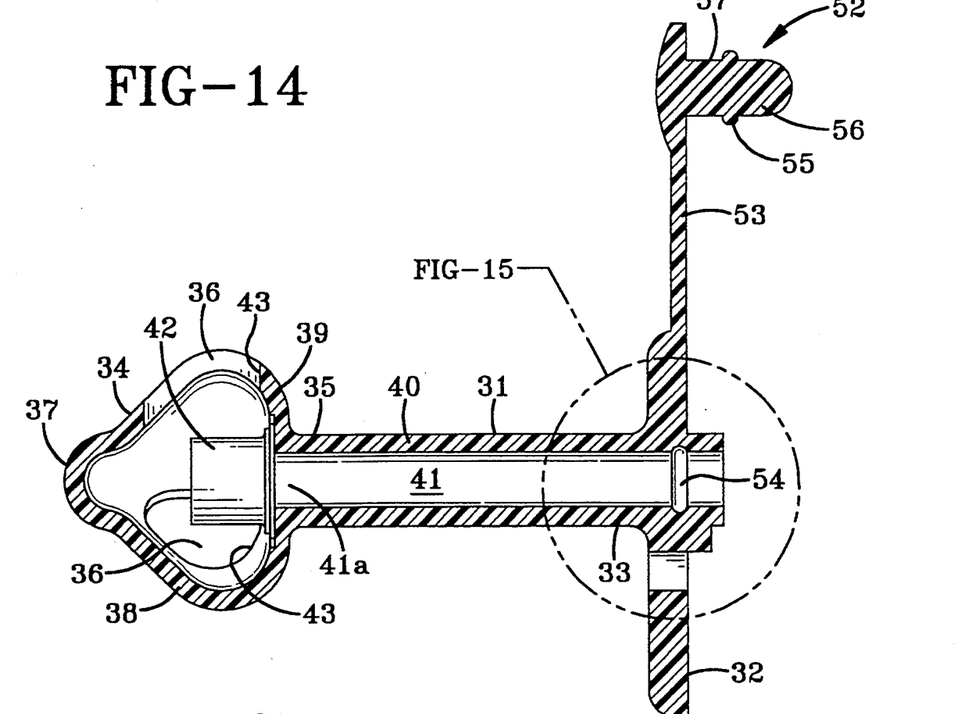
FIG. 14 is a view in longitudinal section of the novel gastrostomy tube of FIG. 11.

Referring now to sectional view FIG. 14 as well as FIG. 1, the dome portion 34 is seen to have an apex 37, a sidewall 38 that is circular in section, and a bottom wall 39 opposite the apex, the bottom wall 39 being substantially planar except for the interruption of the communicating tubular shaft portion 31 and the bottom wall 39 being integrally formed with the sidewall 40 of the shaft portion 31 and substantially planar, although the bottom wall 39 may be adhesively bonded to the shaft portion, if desired. The passageway 41 of the shaft portion 31 communicates with the interior of the dome portion 34, via the present novel one-way valve 42, the cylindrical valve body of which extends into the dome portion from about the bottom wall 39 of the dome portion where the valve is mounted on the inner end 35 of the tubular shaft portion 31.

The tubular shaft portion 31 will ordinarily have a length of from about 1.5 centimeters to about 4.3 centimeters, depending upon the patient in which the device is to be used. The shaft diameter will be in the range of about 18 to about 28 French, i.e., 0.236 to 0.367 inch (6 to 9.3 millimeters).

As seen in FIG. 14, the sidewall 38 of the conventionally shaped dome portion 34 is of uniform thickness from adjacent the apex 37 to the bottom wall 39. The dome portion 34 will generally run about 0.7 to about 0.85 inch (about 17.8 to about 21.6 mm.) in both overall height and width depending on whether the device is intended for use by an adult or child. The dome portion employed is often a bit taller than it is wide. The dome portion is preferably substantially conical in shape.

As seen in FIGS. 11, 12 and 14, the dome portion 34 is provided with three apertures 36 for the egress of fluids fed through the shaft portion 31, although a plurality of two to four or more apertures may be used, if desired. The apertures 36 are preferably oval in shape and substantially equally spaced about the perimeter of the dome portion 34. Wherein these apertures 36 are oval, they each have their major axis lying approximately along a shortest line extending from the apex 37 to the bottom wall 39, with the lowest edge 43 of each aperture 36 adjacent the bottom wall 39 to aid in good fluid movement out of the dome portion, which is an advantage in that little residue of nutrient and other solutions administered are to be found in the dome portion after ordinary rinsing.

The size of the apertures 36 is not sharply critical. The apertures should be large enough to permit ready dissemination of fluids injected through the shaft 31, but not so large as to prevent the dome 34 from performing its retention function, i.e., if there is insufficient sidewall between apertures the sidewall will be overly flexible. Preferably, the apertures are oval with the major axis longitudinal of the dome, the major axis having a length in the range of about 0.3 to about 0.6 inch (7.5 to 15 millimeters) and the minor axis a length in the range of about 0.2 to about 0.4 inch (5 to 10 millimeters) for a dome about 0.65 to 0.8 inch (16.5 to 20.3 millimeters) in height and width. Preferably, the length of the major axis will be in the range of about 0.3 to about 0.5 inch (7.6 to 12.7 millimeters) and the length of the minor axis in the range of about 0.2 to about 0.3 inch (5 to 7.6 millimeters) for a dome in this size range with three apertures.

Figure 14A:
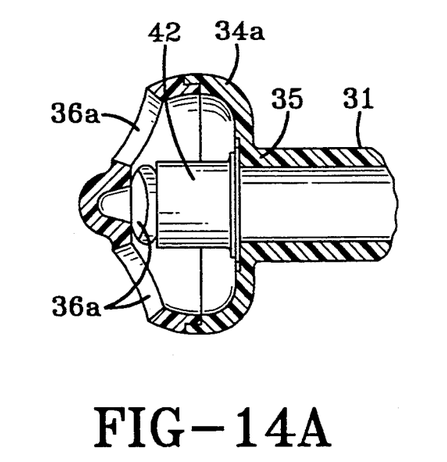
Fig. 14A is a fragmentary portion of a view similar to FIG. 14 showing mainly the dome portion of the gastrostomy device of the invention with a different shaped dome and with the novel valve of the invention mounted therein.

The dome portion may take most any conical or mushroom shape that is circular in section, such as the dome 34a shown in the fragmentary view in section in FIG. 14A. Dome 34a is provided with four apertures 35a evenly spaced about the perimeter of the dome portion. The novel valve 42 is positioned within the dome portion at the inward end 35 of shaft 31.

Figure 15:
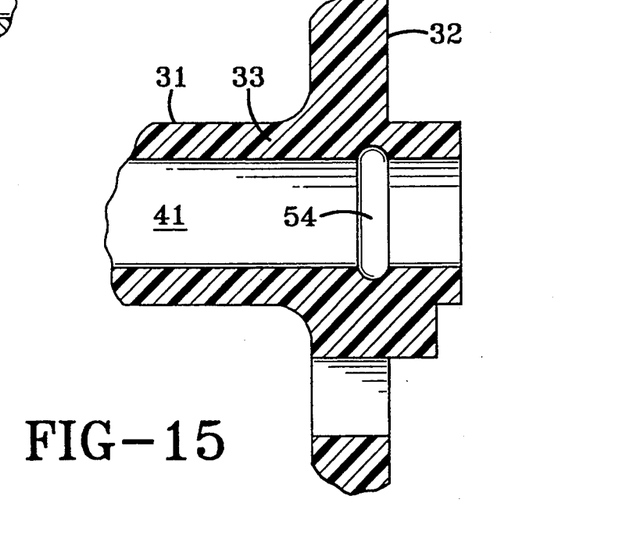
FIG. 15 is an enlarged fragmentary view in section of the portion of FIG. 14 within the circle defined by the broken line.

Referring now to FIGS. 11, 14 and 15, the outward end 33 of the shaft 31 of the gastrostomy tube 30 has integrally formed therewith a retention portion or flange 32 that bears against the skin of the patient when the device is in use and is preferably flat and more preferably triangular so that it can be rotated occasionally for care of the skin surrounding the site. Preferably the flange 32 is perforated a plurality of times, for example three times, about equally spaced around the outer end 33 of the shaft 31 to permit some air to get to the skin surface.

The end 33 of the shaft 31 is conveniently closed by a plug 52. As shown in FIGS. 11-14, the plug 52 is preferably attached to the flange 32 by a flexible membrane or tab 53 to avoid mislaying it. To assure good retention of the plug and a good seal against leakage, the end portion 33 of the shank 31 is preferably formed with an annular groove 54 in the passageway 41 to receive a complementary circumferential ridge 55 on the cylindrical portion 56 of the body 57 of the plug 52.

The one-way valve 42 is a slit valve of the novel design seen in FIGS. 14 and 16-19. The one-way cross-slit valve 42 is seated about the perimeter of the flanged end 49 thereof across the passageway opening 41a at about the bottom wall 39 of the dome portion 34 and provides positive, efficient one-way valve action to prevent reflux of intragastric fluids out of the gastrostomy tube while permitting ready passage of fluids such as nutrients into the stomach of the patient, or, allowing the passage of an obturator during insertion of the device.

The valve 42 is here seen in FIGS. 16-19 to consist of a foreshortened hollow cylindrical body portion 44 having first and second ends 44a and 44b, and within which two substantially identical and mutually intersecting partially folded wall portions, indicated generally by the reference numerals 45 and 45a, each V-shaped in section, are each disposed at a right angle to the other to form a ridge and valley structure in which each wall portion meets, merges and joins with the other at each valley 48, there being four quadrants 47 and four valleys within the hollow cylindrical body portion 44 extending entirely across the passageway of the cylindrical body. The partially folded wall portions 45,45a each extend substantially diametrically of the cylindrical body with the V's both opening in the same axial direction of the cylindrical body 44 i.e., towards the first end, and with the lines or lands 46,46a each formed by a respective apex of a fold line of a partially folded wall portion 45,45a extending along a plane diametrical and substantially normal to the wall of the cylindrical body 44 and each meeting and joining the other land at an angle of about 90 degrees at the center of curvature, i.e., the axis, of the cylindrical body 44 to form four quadrants 47 within the cylindrical body 44. Each wall portion 45,45a ends laterally midway around a quadrant where the wall portion meets, merges and is integrally joined to the other mutually intersecting wall portion to form a valley 48, four valleys in total, that each extend radially outwardly as well as away at an angle, generally, of about 50 to about 65 degrees from the plane in which the apices meet to form the lands 45,45a, extending in the upstream direction of the shaft portion 31, that is, in the direction the valve will not permit fluids to move, which is also in the direction of the flange structure 49 at the first end of the cylindrical body 44. The flange structure 49 facilitates adhesive bonding or otherwise attaching the cylindrical valve body 44 to the inward end 35 of shaft portion 31 with the valve within the hollow dome 34.

By the term foreshortened used with respect to the cylindrical valve body it is meant that the cylindrical valve body is about as wide as it is long.

The surface of each land 46,46a is preferably flat and in said plane and each land is slit entirely through the wall thereof at the intersection thereof with the other land using a sharp instrument to produce very fine intersecting slits 50,50a, each extending along a line about midway of the width of the land surface and about 60 to 80 percent, and preferably about 65 to 75 percent, of the radial length of the land from the intersection 51 of the slits 50,50a to the wall of the cylindrical body 44. The slit lengths are ordinarily in the range of about 1.5 to about 2.5 millimeters.

While the confining presence of the circumferential cylindrical body wall and its hoop strength upon the apices or lands of the ridge and valley structure is highly essential to the non-leaking or very low leakage behavior of the novel cross-slit one-way valve, the width and thickness of the lands is also critical to the one-way valve operation if significant leakage is to be avoided. If the lands are too narrow or too thin, there is not sufficient integrity and serious leakage is likely to occur, while the size requirements of gastrostomy tubes limits the thickness of the folded walls that may be used forming the lands. The width of each land should be, broadly, in the range of about 0.005 to 0.025 inch (0.13 to 0.635 millimeters). Preferably the width of the lands should be in the range of about 0.008 to 0.02 inch (0.20 to 0.50 millimeters), more preferably about 0.01 to about 0.018 inch (0.25 to 0.46 millimeters). The thickness of the lands should be about 0.005 to about 0.030 inch (0.127 to 0.762 millimeter), preferably in the to about 0.025 inch (0.254 to 0.635 millimeter), and more preferably about 0.015 to about 0.025 inch (0.381 to 0.635 millimeter). In other settings the lands may be wider and thicker, for example, up to about 0.25 inch (6.35 millimeters). These dimensions are suitable for the valve when made of silicone rubber and may be increased or decreased somewhat depending on the strength and resiliency of the particular elastomer used in making up the valve, with the lower strength and less resilient elastomers requiring the use of somewhat increased dimensions. Also, in other settings for other uses, especially non-medical uses, the lands may be wider and thicker, if desired, for example, up to about 0.25 inch (6.35 millimeters).

Figure 18:
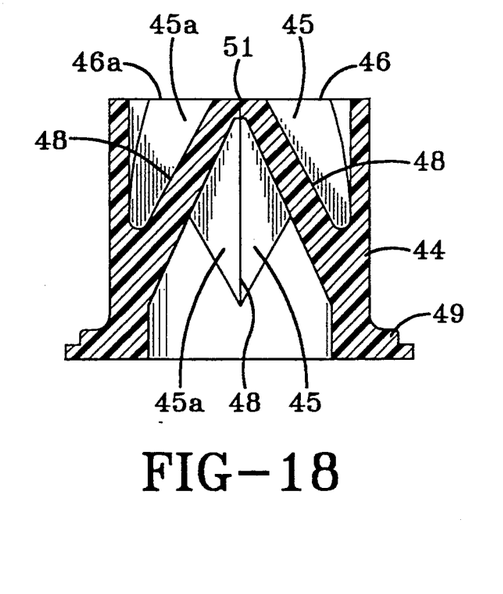
FIG. 18 is a view in section of the valve of FIG. 17 taken in the axial direction along the line 18—18.

Referring now to the sectional view in FIG. 18 there is shown to the left side the integrally formed valley 48 in section at a junction between the respective folded walls 45,45a, then to the rear and in full, the next valley 48, and, to the right side the next valley 48 in section, the folded wall portions 45,45a each being integrally formed with the wall of the cylindrical body portion 44.

Figure 16:
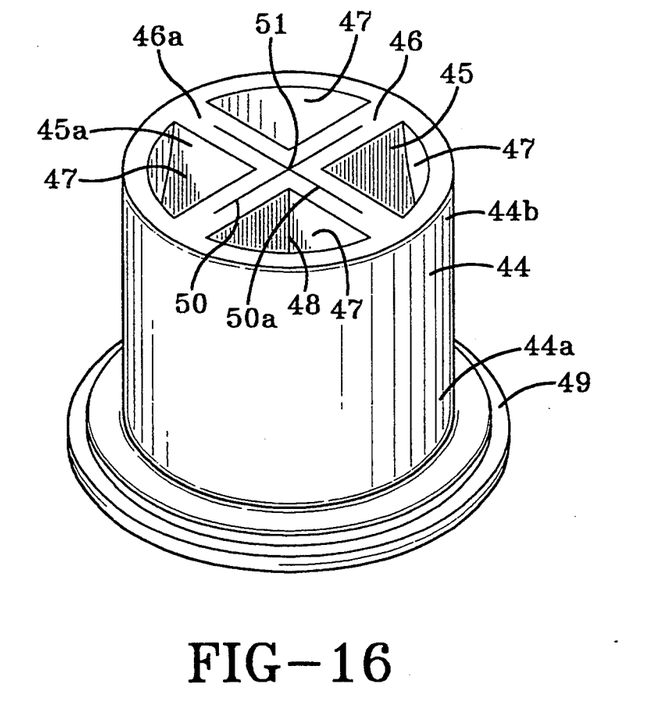
FIG. 16 is an isometric view of the novel one-way cross-slit valve utilized in the present gastrostomy tube and by itself constituting another aspect of the invention, the novel valve being seen as a part of the device shown in FIGS. 11 and 14.
Figure 17:
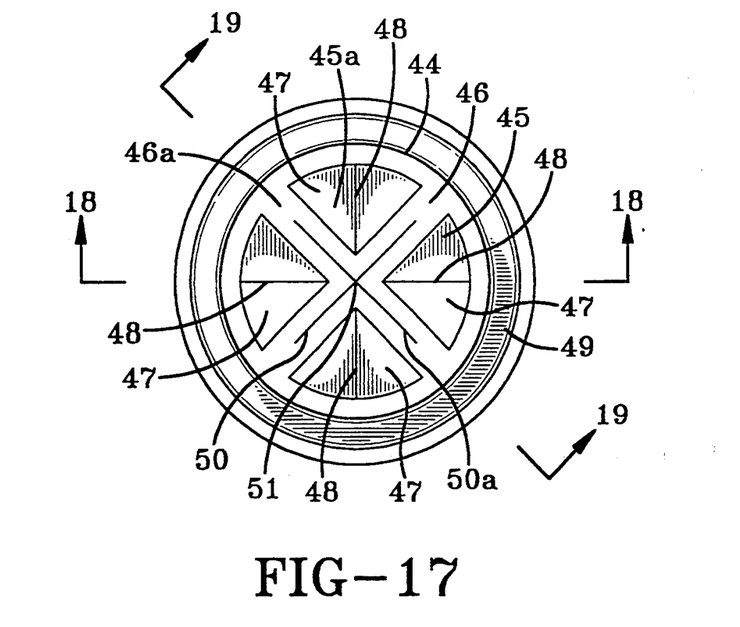
FIG. 17 is a plan view of the valve shown separately in FIG. 16.
Figure 19:
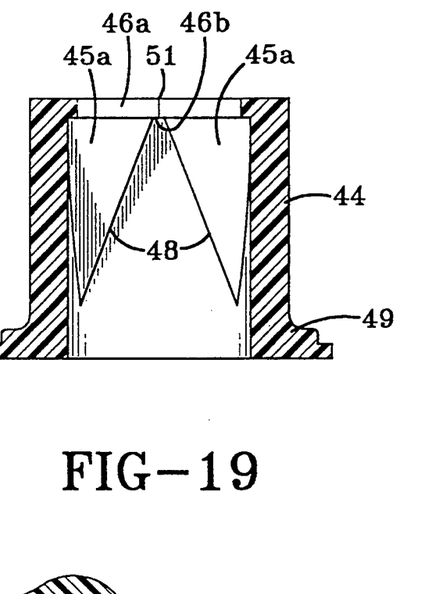
FIG. 19 is a view in section of the valve of FIG. 17 taken in the axial direction along the line 19—19 that lies along a different diameter than followed in FIG. 18, in this case sectioning the land of one of the apices right along the slit therein so that the land does not appear in section except at the unslit portions near the cylindrical body wall.

Referring next to the sectional view in FIG. 19 there is seen a land 46a integrally formed with the wall of the cylindrical body portion 44 and sliced along the line of the sectional view exposing the thickness of the land, the slit 50a, seen also in FIG. 16, not extending the full diametric length of the land 46a. The other land 46 that extends at right angles to the visible land 46a extends out of view back from the intersection 51 of the intersecting slit 50 at mid-width of the visible land 46a. Each valley line 48 demarcates the junction of the folded wall 45a, of which the slitted land 46a is visible in this view, with the companion intersecting folded wall 45 that is hidden in this view. The underside of the land nearly hidden 46 is aligned with the short line at 46b that appears in this view just below the intersecting slit 50 at intersection 51 and between the angularly extending folded wall portions 45a.

This construction of the operative valve portion of the cross-slit duckbill valve gives a very positive one-way valve action, greatly inhibiting the possibilities of reflux of intragastric fluids, while still facilitating the use of an obturator in elongating the dome of the device during insertion through a stoma as well as to accomplish decompression. Additionally, this valve construction permits ready introduction of fluids such as nutrient solutions or slurries. The flange structure 49 also permits 360 degree adhesive attachment of the valve body 44 to the inward end 35 of shaft 31 with resulting significant reduction in the possibility of dislodging the novel slit valve from the end of the shaft as compared to dislodging a conventional, simpler flapper valve which can be attached at one side or end only.

Figure 20:
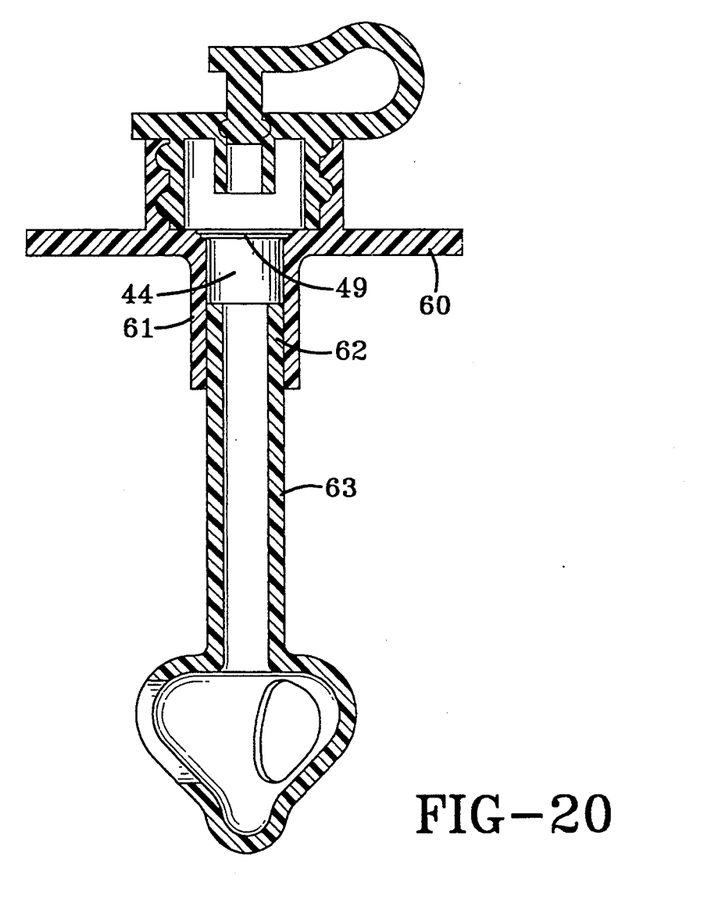
FIG. 20 is a view in section of another embodiment of the present gastrostomy tube wherein the novel valve is positioned at the outer end of the tubular shaft, instead of within the dome.

If desired, the present valve may be utilized in the gastrostomy tube of the invention at the outward end 33 of the shaft 31 instead of within the dome portion 34 at the inward end 35 of the shaft 31. The cylindrical body 44 of the valve may be inserted into the outward end or an end portion large enough to receive the valve body, and the flange structure 49 adhesively bonded to a step provided in the end face of the end 35 of shaft 31. On the other hand, as seen in FIG. 20, the cylindrical body 44 may be fitted into a retention flange 60 having a tubular extension 61 that surrounds and is adhesively bonded to the outward end 62 of shaft 63. The tubular extension 61 is shaped to receive the flange structure 49 of the valve body 44, the flange structure 49 being adhesively bonded to the mouth of the tubular extension.

Figure 6:
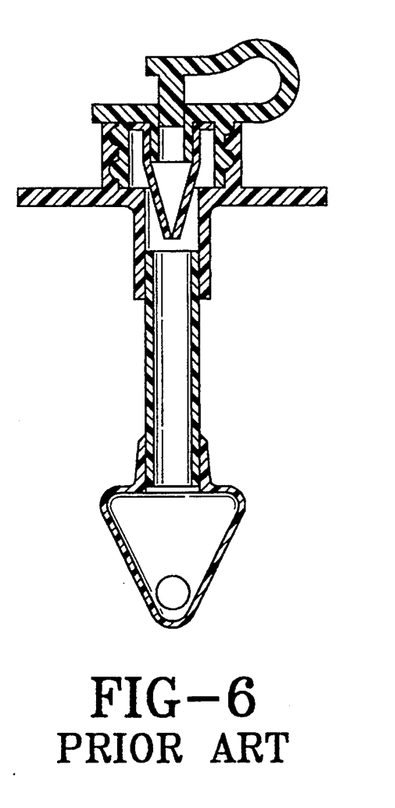
FIG. 6 is a view in longitudinal section of the device of FIGS. 4 and 5 showing that the wall of the dome is of uniform thickness from the apex to the bottom wall, and, that the closure at the inner end of the shaft is a hollow threaded cap fitting within an extension of the retaining element that is attached around the outer end of the shaft, and that there is a simple duckbill valve within the threaded cap, but such valve being without intersecting ridges or slits or any surrounding hoop or cylinder.
Figures 7, 8:
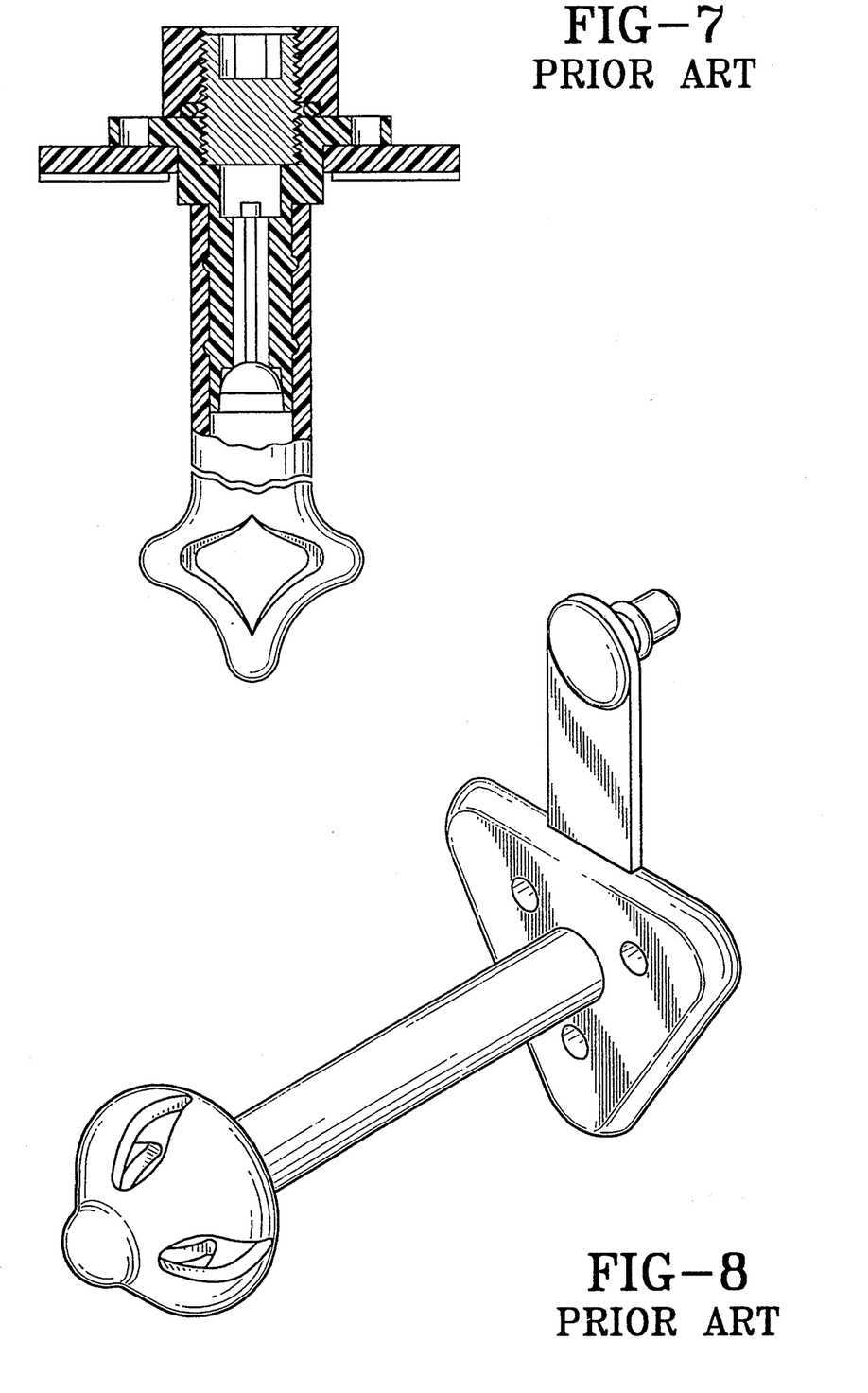
FIG. 7 is a view in longitudinal section of yet another prior art gastrostomy device having a somewhat different shaped dome and with a one-way valve within the shaft and adjacent the dome, the one-way valve having a hemispherical valve element attached to a valve guide and seating into a hemispherical valve seat through which the valve stem extends.
FIG. 8 is an isometric view of yet another prior art low profile gastrostomy device having a hollow shaft with a dome attached at the inner end thereof and a perforated triangular retaining flange at the outer end thereof with an attached plug for closure of the shaft.
Figure 9:
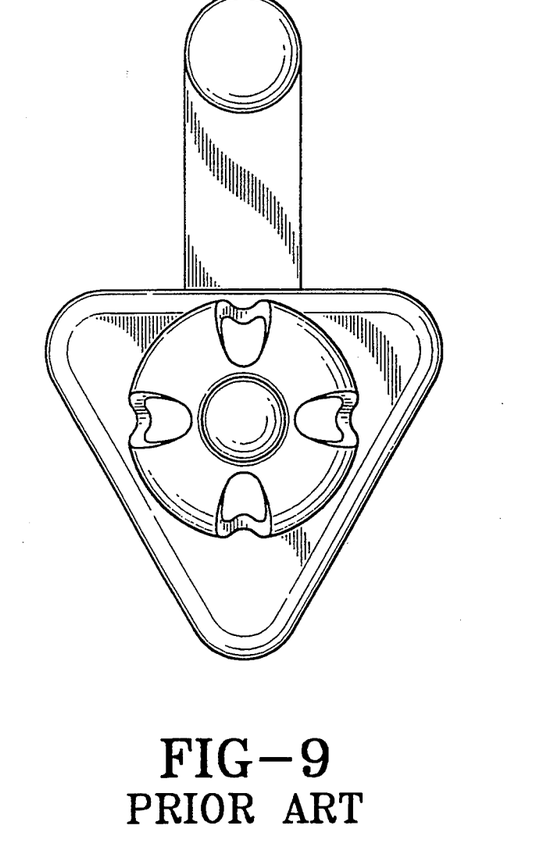
FIG. 9 is a view in end elevation of the device of FIG. 7 showing four apertures or perforations in the wall of the dome and a reinforced apex.
Figure 10:
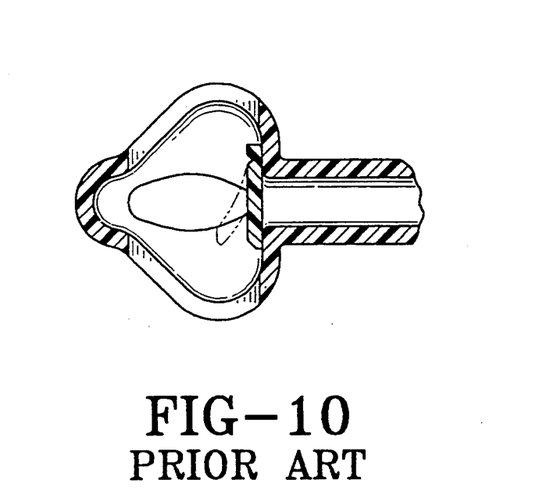
FIG. 10 is a fragmentary view in section of a portion of the inner end of the shaft and the attached dome of the device of FIGS. 8 and 9, showing that the wall of the dome is of uniform thickness from apex to bottom wall and that a flapper valve is used as a one-way valve.

The cylindrical body 44 may also be mounted within the end of an externally threaded cylindrical sleeve such as that shown in the outward end of the device of FIG. 6 and the sleeve threaded into an internally threaded well that communicates with the shaft such as that shown in FIG. 6.

While the one-way cross-slit valve has been described with particular emphasis to its use in gastrostomy tubes, it also finds use in other medical applications in injecting fluids into hollow organs or cavities of the human body where a one-way valve is needed or desired. The one-way cross-slit valve also finds use in non-medical applications where there is a flow of a fluid from a reservoir or other supply means through a tube or supply line up to about 0.25 inch or even 0.5 inch in inner diameter and where one-way valve action is indicated or required. Examples where such valve may be used to advantage include a water supply line to an evaporative still, or a fuel line to a small engine or heater.

We claim:

1. A one-way cross-slit valve formed of an elastomeric material and comprising a foreshortened hollow cylindrical body having first and second ends, a body wall, and an axis and a passageway entirely through the body, the passageway being intercepted by and movement of any fluid therethrough controlled by a transversely extending continuous ridge and valley wall structure, there being two ridges extending substantially diametrically and intersecting at about the axis of the cylindrical body, the ridges constituting apices of folds in the ridge and valley wall structure, and the apices being both slit therethrough the wall at the intersection to provide a cross-slit, the ridge and valley wall structure being integrally formed with and circumferentially confined by the cylindrical body wall whereby the cylindrical body wall provides hoop strength confinement for the apices, and wherein said cross-slit is essentially coplanar with said cylindrical body second end.

2. The one-way cross-slit valve of claim 1 wherein the ridge and valley wall structure comprises two wall portions, each partially folded along a line, the lines each constituting an apex of the partially folded wall, the wall portions being V-shaped in section with the V's opening towards the first end of the cylindrical body and the apices facing the second end of the cylindrical body.

3. The one-way cross-slit valve of claim 2 wherein the apices meet at about the axis of the cylindrical body at about a right angle to each other and substantially within a common plane to form four quadrants, each wall portion ending about midway around a quadrant where it meets and merges and is integrally joined to the mutually intersecting wall portion to form one of the valleys which each extend radially outward from the intersection of the apices.

4. The one-way cross-slit valve of claim 3 wherein the valleys each extend at an angle to the common plane and generally in the direction of the first end of the cylindrical body as well as radially outwardly from the intersection of the apices.

5. The one-way cross-slit valve of claim 4 wherein the apices are flattened to form lands within which the slits are located, the slits crossing at the intersection of the apices.

6. The one-way cross-slit valve of claim 5 wherein the lands are about 0.005 to about 0.25 inch wide.

7. The one-way cross-slit valve of claim 5 wherein the lands are about 0.005 to about 0.025 inch wide.

8. The one-way cross-slit valve of claim 5 wherein the lands are about 0.008 to about 0.02 inch wide.

9. The one-way cross-slit valve of claim 5 wherein the lands are about 0.005 to about 0.030 inch thick.

10. The one-way cross-slit valve of claim 5 wherein the lands are about 0.010 to about 0.025 inch thick.

11. The one-way cross-slit valve of claim 5 wherein the slits are each independently about 1.5 to about 2.5 millimeters in length.

12. A gastrostomy tube comprising a tubular shaft having inner and outer ends and an apertured dome attached at and surrounding the inner end thereof and a one-way cross-slit valve mounted at an end thereof to intercept and control passage of fluid therethrough, the dome having an apex, a bottom wall surrounding the inner end of the tubular shaft and a defining sidewall and being substantially circular in section and the sidewall being substantially uniform in thickness from adjacent the apex to the bottom wall, the one-way cross-slit valve comprising a foreshortened hollow cylindrical body having first and second ends, a body wall and an axis and a passageway entirely through the body, the passageway being intercepted by and movement of any fluid therethrough controlled by a transversely extending continuous ridge and valley wall structure, there being two ridges extending substantially diametrically and intersecting at about the axis of the cylindrical body, the ridges constituting apices of folds in the ridge and valley wall structure, and the apices being both slit therethrough the wall at the intersection to provide a cross-slit, the ridge and valley wall structure being integrally formed with and circumferentially confined by the cylindrical body wall whereby the cylindrical body wall provides hoop strength confinement for the adieus, and, wherein said cross-slit is essentially coplanar with said cylindrical body second end.

13. The gastrostomy tube of claim 12 wherein the dome has three or four apertures about equally spaced about the sidewall.

14. The gastrostomy tube of claim 12 wherein the one-way cross-slit valve is positioned within the dome.

15. The gastrostomy tube of claim 12 wherein a retention flange is attached to and surrounds the outer end of the tubular shaft.

16. The gastrostomy tube of claim 15 wherein the retention flange is integrally molded to the outer end of the tubular shaft.

* * * * *